(12) United States Patent
Bjerregaard et al.

(10) Patent No.: US 12,036,377 B2
(45) Date of Patent: Jul. 16, 2024

(54) HAND-OPERATED FLOW REGULATOR AND ENEMA ADMINISTRATION SYSTEM COMPRISING SAID REGULATOR

(71) Applicant: Qufora A/S, Allerød (DK)

(72) Inventors: Henrik Bork Bjerregaard, Lynge (DK); Ole Hougaard, Helsingør (DK); Lars Monroy, Bagsværd (DK); Kristian Bjerg, Kokkedal (DK)

(73) Assignee: Qufora A/S, Allerød (DK)

( * ) Notice: Subject to any disclaimer, the term of this patent is extended or adjusted under 35 U.S.C. 154(b) by 0 days.

(21) Appl. No.: 18/256,197

(22) PCT Filed: Dec. 7, 2021

(86) PCT No.: PCT/EP2021/084512
§ 371 (c)(1),
(2) Date: Jun. 6, 2023

(87) PCT Pub. No.: WO2022/122699
PCT Pub. Date: Jun. 16, 2022

(65) Prior Publication Data
US 2024/0033417 A1 Feb. 1, 2024

(30) Foreign Application Priority Data
Dec. 11, 2020 (DK) .......................... PA 2020 70824

(51) Int. Cl.
*A61M 3/02* (2006.01)
(52) U.S. Cl.
CPC .......... *A61M 3/022* (2014.02); *A61M 3/0262* (2013.01); *A61M 2205/3334* (2013.01)
(58) Field of Classification Search
CPC ........ A61M 2205/3334; A61M 3/0262; A61M 3/022
See application file for complete search history.

(56) References Cited

U.S. PATENT DOCUMENTS 4,966,551 A   10/1990   Betush
5,882,194 A *   3/1999   Davis .................... A61C 1/088
                                                                                433/91

(Continued)

FOREIGN PATENT DOCUMENTS

| GB | 2166222 | 4/1986 |
|----|---------|--------|
| WO | 2011/023196 | 3/2011 |
| WO | 2015/117104 | 8/2015 |

OTHER PUBLICATIONS

International Search Report and Written Opinion for International PCT Patent Application No. PCT/EP2021/084512 mailed Mar. 28, 2022 (9 pages).

*Primary Examiner* — Theodore J Stigell
*Assistant Examiner* — Rachel T. Smith
(74) *Attorney, Agent, or Firm* — Fox Rothschild LLP (57) ABSTRACT

A hand-operated flow regulator is adapted to be inserted between an elastomeric bulb pump and a tubing as a part of an enema flow path. The hand-operated flow regulator comprises a main flow body, and a tubular pump coupling end part having a free pump coupling end and defining a first flow section. The tubular pump coupling end part extends via an exterior regulator body part into a tubular tube coupling end part having a free tube coupling end and defining a second flow section. An interior regulator body part is situated rotatable and substantially coaxially inside the exterior regulator body part, and a pivotable grip is in operative communication with the interior regulator body part to open and close the enema flow path.

32 Claims, 7 Drawing Sheets

(56) References Cited

U.S. PATENT DOCUMENTS

| | | |
|---|---|---|
| 11,661,929 B1 * | 5/2023 | Campbell ............ A61M 1/741 604/35 |
| 2006/0033066 A1 | 2/2006 | Carrez et al. |
| 2010/0087792 A1 | 4/2010 | Nielsen et al. |
| 2012/0143168 A1 * | 6/2012 | Bjerregaard ........ A61M 3/0295 604/257 |
| 2012/0259300 A1 | 10/2012 | Bjerregaard |
| 2017/0122443 A1 | 5/2017 | Arguello |
| 2017/0273756 A1 * | 9/2017 | Thomas ................ A61C 17/14 |
| 2020/0390961 A1 * | 12/2020 | Zhang ................ A61M 3/0279 |

* cited by examiner

HAND-OPERATED FLOW REGULATOR AND ENEMA ADMINISTRATION SYSTEM COMPRISING SAID REGULATOR

This application is a 371 filing of International Patent Application PCT/EP2021/084512 filed Dec. 7, 2021, which claims the benefit of PA 2020 70824 filed Dec. 11, 2020.

TECHNICAL FIELD

The present invention relates to a flow regulator for use in an enema in combination with an elastomeric bulb pump to inject an enema into an individual, such as an individual in need of intestinal irrigation. The hand-operated flow regulator is adapted to be inserted between an elastomeric bulb pump and an enema supply tubing as a part of an enema flow path. The flow regulator comprises a main flow body having
  a main flow regulator axis,
  a tubular pump coupling end part having a free pump coupling end and defining a first flow section,
  the tubular pump coupling end part extends via an exterior regulator body part into a tubular tube coupling end part having a free tube coupling end and defining a second flow section, and
  an interior regulator body part is situated rotatable and substantially coaxially inside the exterior regulator body part.

As used herein the term "enema administration" is used in its conventional understanding and refers to a procedure in which a liquid, the enema, is injected into the lower bowel by way of the rectum for cleansing the bowels and/or relieving constipation. The "enema" can e.g., be water or saline.

BACKGROUND

Flow regulators that more or less squeeze the enema supply tubing together to adjust the flow of enema are known in the art. Such flow regulators can for example be of the so-called roller type known from intravenous drips. By operating a roller in an inclined track of a housing mounted surrounding the enema supply tubing the flow of enema can be increased or decreased. The enema tubing is however rather thick and operating the roller properly along the tubing is cumbersome.

Furthermore, it is preferred to operate an enema administration system using just one hand. The irrigation catheter is inserted in rectum to allow the enema to flow into the lower bowel via the rectum. Then the elastomeric bulb pump must be operated to inject the required amount of enema. Coordination of pumping and adjusting flow rate of enema is a huge challenge for the individual who is placed in a very awkward position when having the irrigation catheter inserted in the rectum.

A simple flow regulator is known from the applicant's international patent application WO2011023196A1. This known flow regulator comprises a housing and a rotatable cylinder placed inside the housing. The cylinder rotates in the housing by means of a turning knob. However some people find it difficult to operate a turning knob by just one hand in order to properly regulate passage of enema liquid through the flow regulator.

SUMMARY OF THE INVENTION

It is a main aspect of the present invention to provide a flow regulator for use in an enema administration in combination with an elastomeric bulb pump, which flow regulator is easier to operate during the enema administration than hitherto known.

In a further aspect is provided a flow regulator that can be operated during an enema administration by the same hand that simultaneously operates an elastomeric bulb pump.

In a further aspect is provided a reliable flow regulator for opening and closing for the flow of enema during an enema administration.

In a further aspect is provided a reliable flow regulator for preventing backflow of injected enema into the elastomeric bulb pump during an enema administration.

In a further aspect of the present invention is provided a flow regulator, the operation of which does not require visual sight during operation.

In a further aspect of the present invention is provided a flow regulator that has tactile operating means.

In a further aspect of the present invention is provided an enema administration system comprising an elastomeric bulb pump and a flow regulator coupled to the elastomeric bulb pump at a distance from said elastomeric bulb pump, wherein both the flow regulator and the elastomeric bulb pump can be reached and operated by same hand during the enema administration.

In a further aspect of the present invention is provided an enema administration system comprising an elastomeric bulb pump and a flow regulator configured to be directly coupled to said elastomeric bulb pump.

The novel and unique features whereby these and other aspects are achieved according to the present invention consist in that the flow regulator comprises a pivotable grip in operative communication with the interior regulator body part to open and close the enema flow path, wherein the pivotable grip moves lengthwise along the main flow regulator axis.

By making the flow regulator part of the enema flow path by inserting it between an elastomeric bulb pump and an enema supply tubing instead of external to the tubing the individual need not use a lot of force to squeeze an enema supply tubing, or manipulate a flow regulator by one hand at the same time as pumping the elastomeric bulb pump with the other hand, because the flow regulator is situated a long distance from the elastomeric pump to be reachable by said other hand. It is thus not preferred to have the flow regulator remote from the elastomeric bulb pump because this position would require two-handed operation.

The flow regulator may advantageously be secured at the downstream end of the elastomeric bulb pump, thus to the tubing at the enema delivery end of the elastomeric bulb pump opposite the enema receiving end of said pump, which enema receiving end is connected to an enema reservoir.

The function principle of the flow regulator resembles the shut off valve function principle of a ball valve, however the flow regulator of the current invention does not utilize a ball but an interior regulator body part that is situated rotatable and substantially coaxially inside the exterior regulator body part.

The pivotable grip is provided in operative communication with the interior regulator body part to open and close the enema flow path. The pivotable grip can be operated manually from outside the main flow body by means of a pivotable grip in operative communication with the interior regulator body part.

The pivotable grip moves lengthwise along the main flow regulator body, so that it is minimum in the way during maneuvers, and so that it can be operated while holding e.g., a single operating finger in same location during the entire enema administration. The pivotable grip is thus easily accessible and easy to operate from outside the main flow body. By pivoting the pivotable grip the interior regulator body part can be turned a selected angle in opposite directions, e.g., 90° or less, such as 88°, 85°, or 83°, around its rotation axis, to allow enema to flow through, or to block the flow of enema. Preferably the turning of the pivotable grip is stepless, however turning may be stepped.

The flow regulator may advantageously be secured at the downstream end of the elastomeric bulb pump, thus to the tubing at the enema delivery end of the elastomeric bulb pump opposite the enema receiving end of said pump, which enema receiving end is connected to an enema reservoir. Thus the free pump coupling end part may couple to the inspiration end of the elastomeric bulb pump, preferably through a valve member, and the opposite tubular tube coupling end part may serve to couple to the enema tubing that is connected to a reservoir of suitable enema.

Advantageously the exterior regulator body part may be configured as an exterior cylinder delimited by an exterior cylinder wall and having an exterior cylinder axis substantially perpendicular to the main flow regulator axis to thereby make the interior regulator body part that is arranged turnable inside the exterior regulator body part easy to couple to the pivotable grip.

The exterior cylinder may e.g., have a first exterior cylinder end opposite a second exterior cylinder end disposed protruding on each their long sides of the main flow body. The exterior cylinder may be disposed substantially at the middle of said main flow body or slightly offset said middle, to be easily accessible at a short distance from the elastomeric pump, such as be accessible by the hand used to operate said elastomeric pump.

The first flow section and the second flow section may have substantially the same length or different length to provide sufficient coupling length to the respective other component to which the flow regulator is to be coupled, and lengths that provide sufficient distance from the elastomeric pump for the pivotable grip to pivoted without any hitting obstructions.

The exterior cylinder wall may have a first opening opposite the free pump coupling end and a second opening opposite the free tube coupling end, which first opening extends into the first flow section, and which second opening extends into the second flow section. The first opening and the second opening enable flow of enema through the exterior cylinder when the pivotable grip is arranged in open position.

The interior regulator body part may be an interior cylinder delimited by an interior cylinder wall, and having an interior cylinder axis coaxially aligned with the exterior cylinder axis, to be rotatable inside the exterior cylinder about a common central axis.

Advantageously the exterior diameter of the interior cylinder corresponds substantially to the interior diameter of the exterior cylinder, whereby the exterior surface of the interior cylinder rotates in contact with the interior surface of the exterior cylinder, and whereby the central axis of the interior cylinder and the central axis of the exterior cylinder can be kept coaxial during the rotating movement.

The interior cylinder may have a first interior cylinder end opposite a second interior cylinder end. The first interior cylinder end may be in substantially the same plane as the first exterior cylinder end, or close to said first exterior cylinder end. The second interior cylinder end may be in substantially the same plane as the second exterior cylinder end, or close to said second exterior cylinder end.

The interior cylinder advantageously accommodates a diametrically arranged flow pipe through which enema liquid can pass when the interior cylinder is turned appropriately in relation to the exterior cylinder.

The flow pipe may have a first pipe opening opposite a second pipe opening, which first pipe opening and second pipe opening are located in the interior cylinder wall to obtain a flow path through the interior cylinder and the exterior cylinder.

Due to first pipe opening and second pipe opening the flow path through the interior cylinder is alignable with the first opening and the second opening of the exterior cylinder by operating the pivotable grip to pivot the interior cylinder, thereby providing a more or less open enema flow path for performing an enema. By the reverse pivoting of the pivotable grip the interior cylinder is arranged turned away from said alignment and the interior cylinder wall blocks the enema flow path whereby the enema administration is fully stopped or temporarily stopped.

In order for the interior cylinder to rotate, the first interior cylinder end may have a first cylinder coupling means configured to lock together with a first grip coupling means of the pivotable grip.

The second interior cylinder end may have a second cylinder coupling means configured to lock together with a second grip coupling means of the pivotable grip.

So the pivotable grip may be secured to the interior cylinder at one or both of the interior cylinder ends.

The interior cylinder may then be arranged inside the exterior cylinder to be pivoted between a fully open flow position in which the first pipe opening is aligned with the first opening in the exterior cylinder wall, and the second pipe opening is aligned with the second opening in the exterior cylinder wall, and a fully closed position in which none of said pipe openings are aligned with any of said first and second openings. Any intermediate opening position can be achieved by holding the pivotable grip in a position between the fully open and the fully closed position.

For the pivotable grip to be easy to grasp, manipulate and operate the pivotable grip may have a U-bend handle part, which U-bend handle part conveniently may have opposite free ends provided with a respective one of the first grip coupling means and the second grip coupling means. The U-bend handle part protrudes from the main body part, so that it is easy to contact. Moreover the U-bend shape has no sharp edges, so that the pivotable grip has a smooth exterior and cannot hurt the surrounding tissue even at a vulnerable site as when close to the anus.

Preferably said first grip coupling means and said second grip coupling means can be male coupling means and/or female coupling means. Preferably said first grip coupling means and said second grip coupling means may be configured as coupling means selected from the group comprising snap fittings, hooking means, catch pins, turning holes or combinations thereof.

The first cylinder coupling means and the second cylinder coupling means may be male coupling means and/or female coupling means adapted to couple to respective complementary first grip coupling means and second grip coupling means in form of female coupling means and/or male coupling means.

Preferably said first cylinder coupling means and second cylinder coupling means can be selected from the group comprising snap fittings, hooking means, keyways or combinations thereof.

Preferably the first grip coupling means and the second grip coupling means that engage and interlock with the first cylinder coupling means and the second cylinder coupling means, respectively, may be dimensioned so that the first grip coupling means covers the first interior cylinder end and the first exterior cylinder end, and the second grip coupling means covers the second interior cylinder end and the second exterior cylinder end, so that no foreign bodies can enter any of the interior cylinder and the exterior cylinder, or enter the interface between said interior cylinder and exterior cylinder that could obstruct or jam turning the interior cylinder by pivoting the pivotable grip.

The first exterior cylinder end may have a first pivot stop, and the first interior cylinder end may have a second pivot stop that engages the first pivot stop to restrict a pivot angle of the pivotable grip so that the handle part, such as the U-bend handle part, does not get too close to the main flow is too difficult to grasp and hold onto in order to be operated by the same hand as used to squeeze and relieve pressure on the elastomeric bulb pump. Accordingly, the co-operating first pivot stop and second pivot stop serve to restrict the possible pivot angle of the pivotable grip when the enema flow path are to be opened and closed as the need requires. The pivot angle of the pivotable grip may correspond to the rotation angle of the interior cylinder between an open position wherein the flow pipe axis is fully aligned with the first opening and the second opening, and a closed position wherein the flow pipe axis is rotated so that the first pipe opening and the second pipe opening are brought fully away from the first opening and the second opening and is blocked by the exterior cylinder wall.

The first pivot stop can e.g., be an angular track provided circumferentially on the first exterior cylinder end.

Preferably the second pivot stop can be a protrusion extending from the interior cylinder wall parallel to the exterior cylinder axis along an angular section of the circumference of first interior cylinder end which is shorter than the angular track on the first exterior cylinder end, whereby the protrusion can move from side to side along the angular track.

The freedom to rotate the interior cylinder in relation to the exterior cylinder is defined by the difference between the angular length of the angular track and the angular length of the protrusion. Said difference is constituted by a sector of a circle which defines the possible pivot angle of the interior cylinder in relation to the exterior cylinder that serves for opening and closing the enema flow path through the flow regulator. The protrusion expediently can move from side to side within the angular track but not out of said angular track.

A backflow preventer means that serves to avoid backflow from injected enema into the flow regulator or the elastomeric bulb pump may be part of the flow regulator.

The backflow preventer means may e.g., be inserted in the first flow section. Any kind of non-return valve may be a suitable backflow preventer means that serves to prevent pressure loss and backflow between pumping cycles of the enema administration.

The back flow preventer means may accommodate a valve ball or bead, and may have an enema inlet, which faces the exterior regulator body, and an opposite enema outlet, which enema inlet may be traversed by a crossbar configured to prevent the valve ball from being sucked inside the flow regulator when the elastomeric pump is operated.

Preferably the back flow preventer means is tubular to be easily inserted and fitted inside e.g., the tubular pump coupling end part.

The flow regulator may be provided with a finger support member that protrudes axially spaced apart from the main flow body along the main flow regulator axis to assist in operation when the pivotable grip is to be operated. The finger support member may advantageously serve as a finger abutment or finger grasping element so that the finger(s) that operates the pivotable grip does not slip during turning of said grip.

To provide space for the abutting finger the finger support member may be arranged with a gap to the exterior cylinder.

The finger support member may conveniently be arranged above the exterior regulator body part and have an exterior face having tactile indicator means, whereby the user very easily can verify that the position of the hand-operated flow regulator is correct prior to use.

The finger support member may advantageously be shaped as a bridge member having opposite bridge ends secured to the tubular pump coupling end part and the tubular tube coupling end part, respectively, thereby extending above the exterior regulator body part so that it does not obstruct turning of the pivotable grip.

The tactile indicator means may be a row of elevations whereby the user easily can establish the pivot angle of the pivotable grip by feeling the elevations with the fingers.

Establishing the pivot angle of the pivotable grip by feeling the elevations with the fingers elevations is especially easy if the elevations of the row of elevations have gradually reduced sizes.

The fingers elevations may e.g., be disc-shaped and the discs have gradually reduced sized diameters along the length of the finger support member. The elevation having the largest diameter may e.g., be the elevation providing the largest flow through the flow regulator, e.g., a fully open flow path. Similarly the elevation having the smallest diameter may be the elevation providing no flow through the flow regulator, e.g., a fully closed flow path.

The invention further relates to an enema administration system comprising an elastomeric bulb pump, an irrigation catheter, and the above-mentioned hand-operated flow regulator of the present invention.

Preferably is the free pump coupling end part of the hand-operated flow regulator coupled directly to an inspiration end of the elastomeric bulb pump. A tubing is secured to the tube coupling end part and has it opposite end secured to a source of enema, thereby establishing an enema flow path through the flow regulator and the elastomeric bulb pump.

BRIEF DESCRIPTION OF THE DRAWING FIGURES

The invention will now be described in further details with reference to the drawing in which.

DETAILED DESCRIPTION OF THE INVENTION

Figure 1:
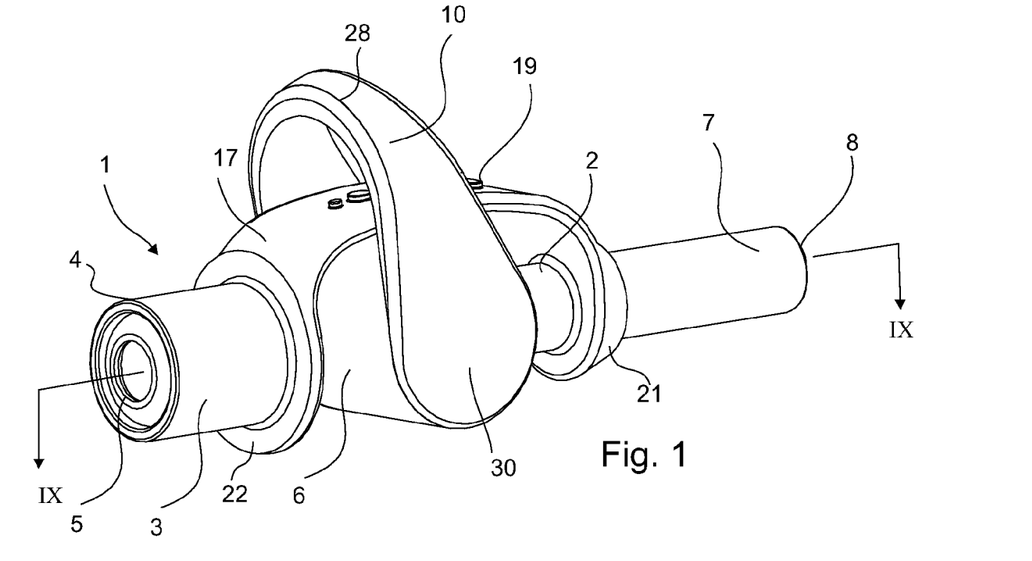
FIG. 1 is a perspective side view of an embodiment of a flow regulator of the present invention seen from the pump coupling end part and with a closed enema flow path.
Figure 2:
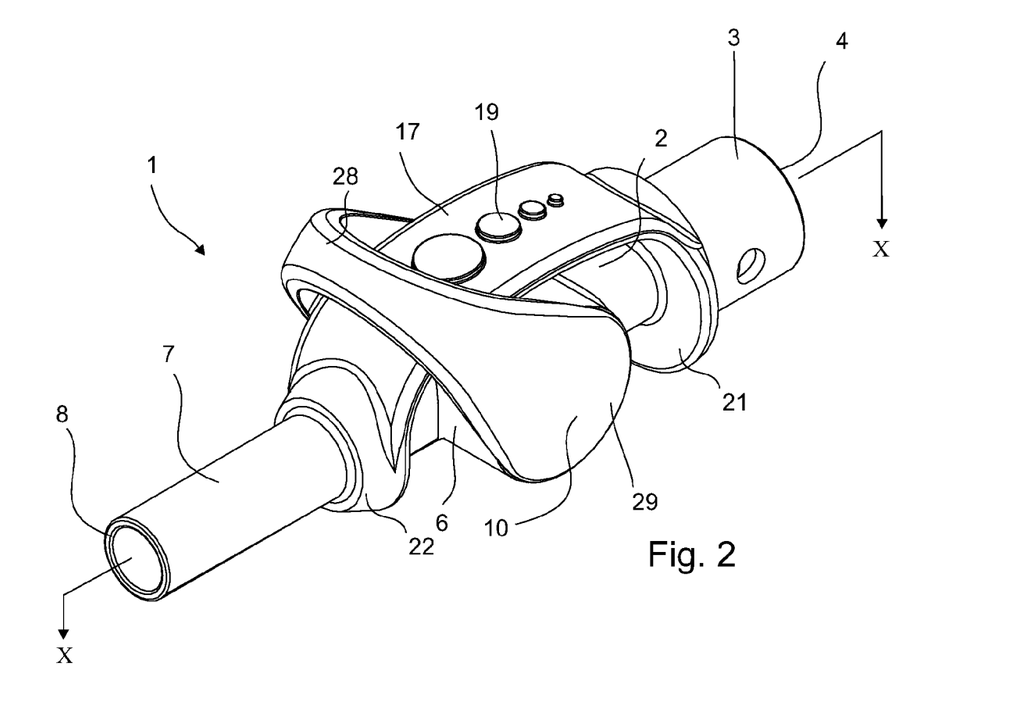
FIG. 2 shows the same seen from the tube coupling end part and with an open enema flow path.

FIGS. 1 and 2 are perspective side views of an exemplary embodiment of a flow regulator 1 with open and closed enema pathway, respectively. The flow regulator 1, which is shown in FIG. 1 in closed position, is seen in exploded views in FIGS. 3 and 4 from different sides.

The flow regulator 1 has a main flow body 2 having a main flow regulator axis A that also is the central axis of the enema flow path. Said main flow body 2 has a tubular pump coupling end part 3 in which a back flow preventer in form of a non-return valve 5 is inserted. The tubular pump coupling end part 3 has a free pump coupling end 4 and delimits a first flow section F1. The tubular pump coupling end part 3 extends via an exterior regulator body part 6 into a tubular tube coupling end part 7 having a free tube coupling end 8 and defining a second flow section F2.

The flow regulator 1 also comprises an interior regulator body part 9, which is situated substantially coaxially inside the exterior regulator body part 6, and a pivotable grip 10 in operative communication with the interior regulator body part 9 to open and close the enema flow path.

Figure 3:
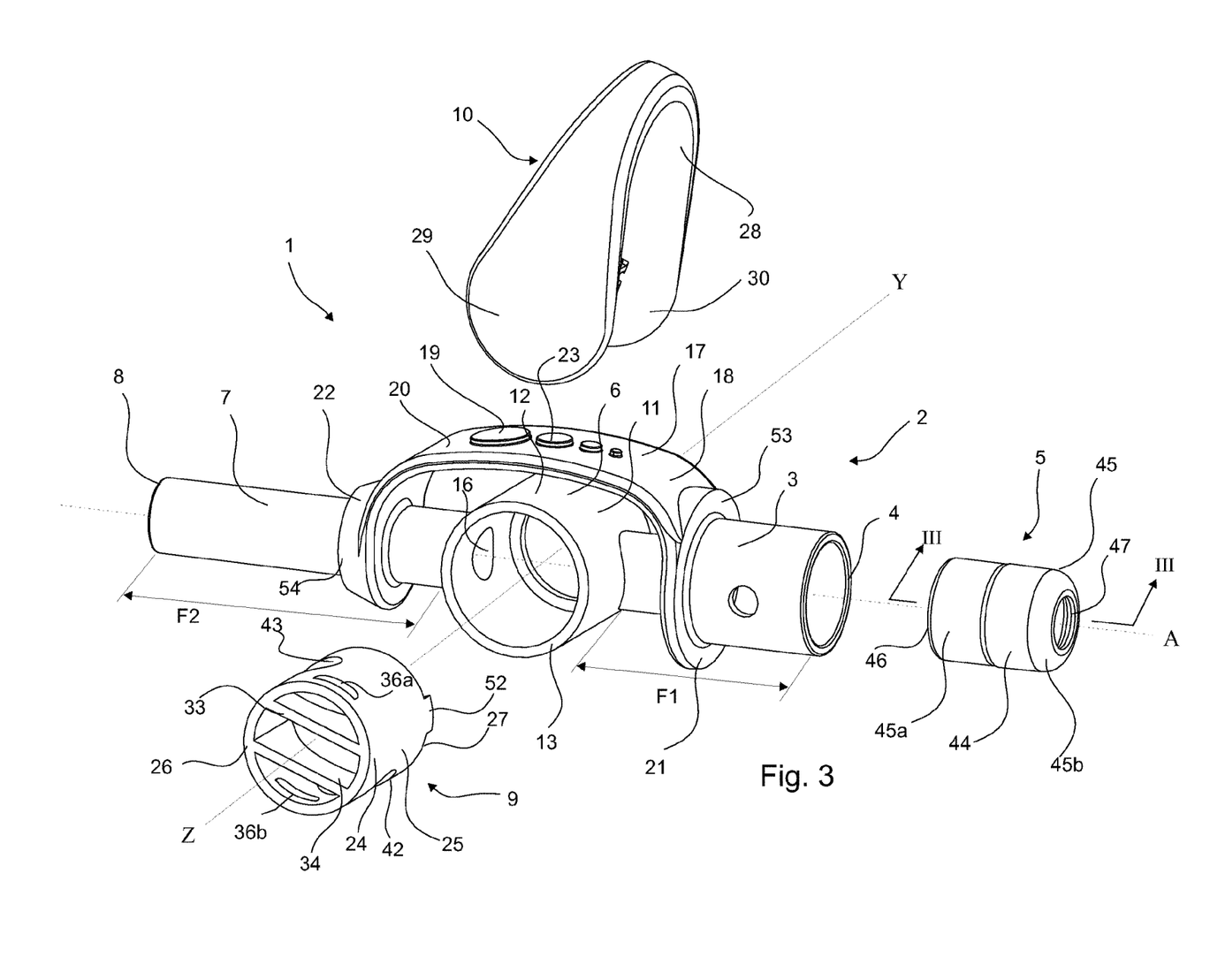
FIG. 3 is an exploded view of the same seen from the second interior cylinder side.
Figure 4:
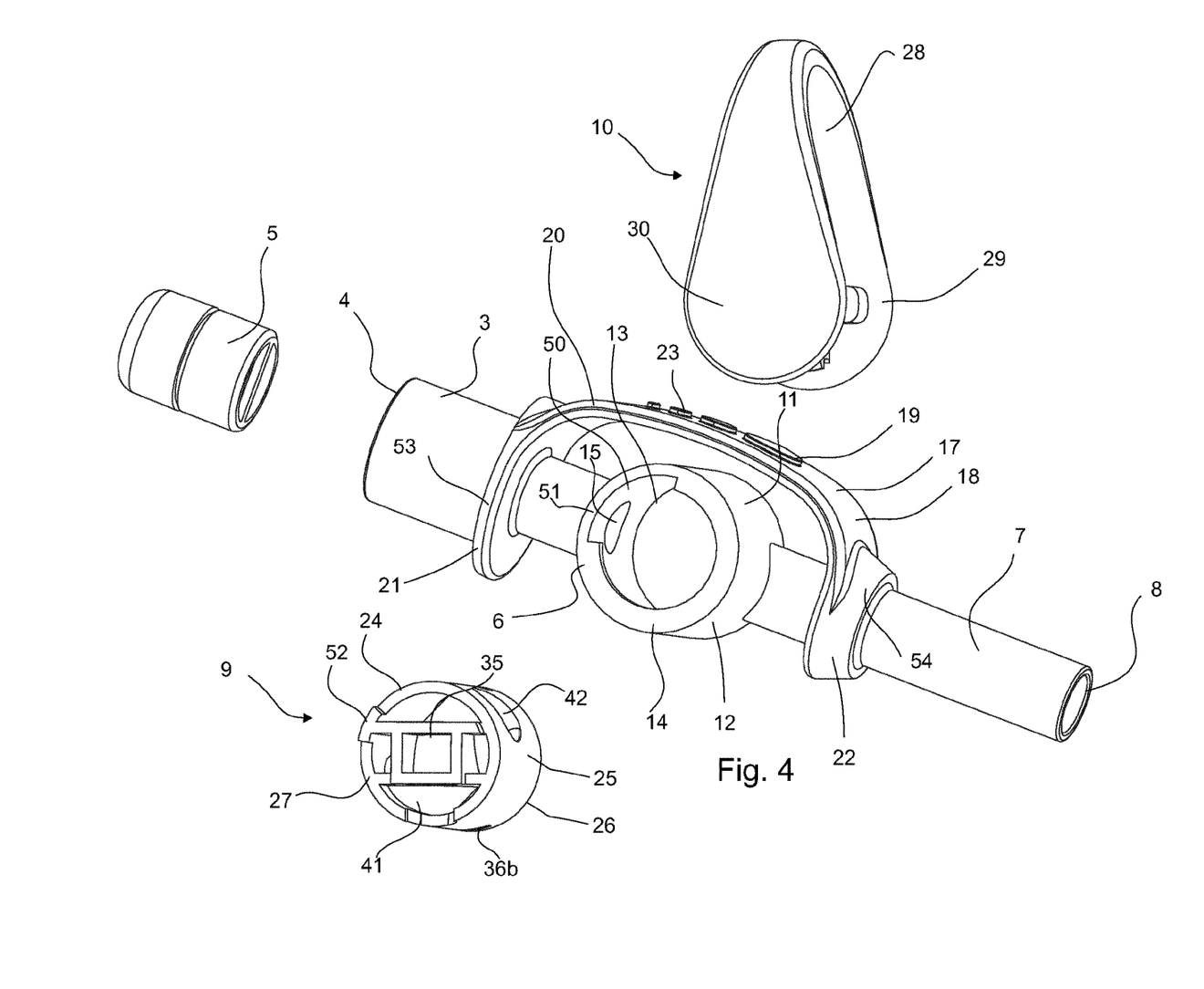
FIG. 4 shows is an exploded view of the same seen from the first interior cylinder side.

In FIGS. 1, 3 and 4 the pivotable grip 10 is in a position wherein it is pivoted towards the tubular pump coupling end part 3 whereby the enema flow path through the main flow body 2 is closed. In FIG. 2 the enema flow path through the main flow body 2 is open.

The exterior regulator body part 6 has an exterior cylinder wall 12, and a first exterior cylinder end 13 opposite a second exterior cylinder end 14. The exterior regulator body part 6 is further configured as an exterior cylinder 11 having an exterior cylinder axis Y substantially perpendicular to the main flow regulator axis A.

The exterior cylinder wall 12 has a first opening 15 that extends into the first flow section F1 opposite the free pump coupling end 4, and a second opening 16 which extends into the second flow section F2 opposite the free tube coupling end 8. The first opening 15 and the second opening 16 are aligned along the main flow regulator axis A and constitute openings in the enema flow path.

A finger support member 17 protrudes above the exterior regulator body part 6 and exposes an exterior face 18 having tactile indicator means 19 that enables the individual who performs an enema administration to have a further tactile verification means to verify which direction to move the pivotable grip 10 to open and close the flow regulator 1, as well as to verify whether the flow regulator 1 already is open or closed.

In the exemplary embodiment of a flow regulator 1, the finger support member 17 is shaped as a bridge member 20 having opposite bridge ends 21,22 mounted to the tubular pump coupling end part 3 and the tubular tube coupling end part 7, respectively, in a manner so that the bridge member 20 extends above the exterior regulator body part 6 with the opposite bridge ends 21,22 secured to the aforesaid respective coupling parts 3,7. The tactile indicator means 19 is in the present embodiment configured as a row of elevation 23 having gradually reduced sizes. In the present embodiment the elevations 19 are exemplified as four small discs, wherein the largest elevation has a diameter of about 6 mm, the second largest elevation has a diameter of about 3 mm, the third largest elevation has a diameter of about 2 mm, and the smallest elevation has a diameter of about just 1 mm. The configuration, the dimensions and the attachment of the finger support member 17 to the main flow body 2, as well as the configuration, the dimensions, the positions, and the attachment of the tactile indicator means 19 to the bridge member 20 are just one example of many possible designs. This shown exemplary embodiment should not be construed as limiting the scope of the present invention in respect of finger support member 17 and tactile indicator means 19. For example can the finger support member 17 be integral with the main flow body 2, whereby there is no gap between said finger support member 17 and the main flow body 2. Alternative tactile indicator means can for example be depressions, rings, ribs or grooves extending crosswise and/or lengthwise the bridge member 20. Some embodiments may not have a finger support member 17 at all.

The interior regulator body part 9 is configured as an interior cylinder 24 having an interior cylinder axis Z coaxially aligned with the exterior cylinder axis Y. The interior regulator body part 9 has an interior cylinder wall and a first interior cylinder end 26 opposite a second interior cylinder end 27.

Figure 5:
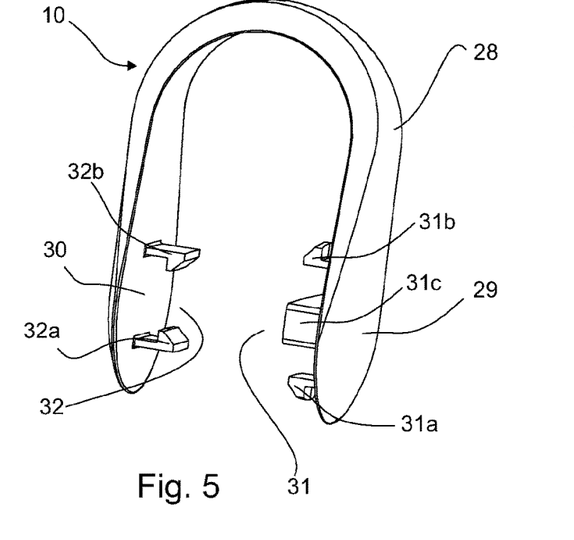
FIG. 5 is a front, inclined, perspective view of the pivotable finger grip.

The pivotable grip 10, which is also seen in an enlarged scale view in FIG. 5, has a U-bend handle part 28 with opposite enlarged free ends 29,30, each having a respective one of the first grip coupling means 31 and the second grip coupling means 32, and each having a substantially circular outline to more or less cover any of the first interior cylinder end 26, the second interior cylinder end 27, the first exterior cylinder end 13 and the second exterior cylinder end 14.

Correspondingly, the first grip coupling means 31 is constituted by two slightly flexible first hooks 31a,31b and a catch bar 31c disposed between said flexible first hooks 31a,31b, as seen in FIG. 5. The flexible first hooks 31a,31b are arranged to connects to a first cylinder coupling means 33, seen in FIG. 3, at the first interior cylinder end 26 of the interior cylinder 24, when the catch bar 31c, which is positioned in-between and spaced apart from the flexible first hooks 31a,31b, is placed in a catch opening 34 of the first cylinder coupling means 33, to thereby lock together with the interior cylinder 24, and carry said interior cylinder 24 along when the pivotable grip 10 is pivoted.

The second grip coupling means 32 is constituted by two slightly flexible second hooks 32a,32b, as seen in FIG. 5. The flexible second hooks 32a,32b are arranged to hook into a second cylinder coupling means 35, seen in FIG. 6, at the second interior cylinder end 27 of the interior cylinder 24.

In addition to the catch opening 34 that accommodates the catch bar 31c, the first cylinder coupling means 33 is composed of two diametrically opposite first coupling openings 36a,36b in the interior cylinder wall 25 at the first interior cylinder end 26, for hooking by the flexible first hooks 31a,31b.

The second cylinder coupling means 35 has a guide member 38 extending inside the interior cylinder 26. The guide member 38 is delimited by a guide wall 39 having opposite second coupling openings 40a,40b retracted from the second interior cylinder end 27, as seen in FIG. 6, whereby said opposite second coupling openings 40a,40b are positioned to lock together with the flexible second hooks 32a,32b of the second grip coupling means 32, when said flexible second hooks 32a,32b are guided inside the lumen of the guide member 38.

Figure 7:
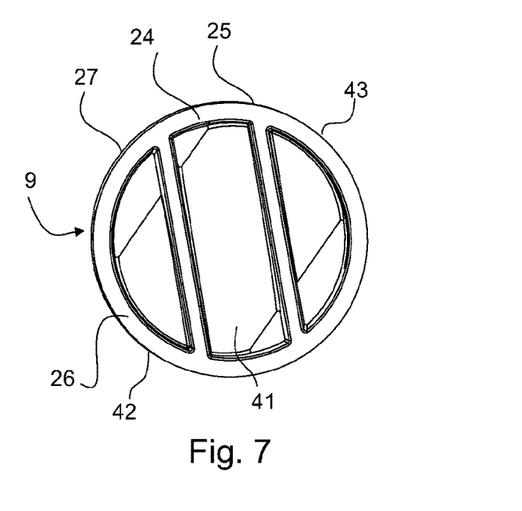
FIG. 7 shows the same seen from the first interior cylinder end.
Figure 9:
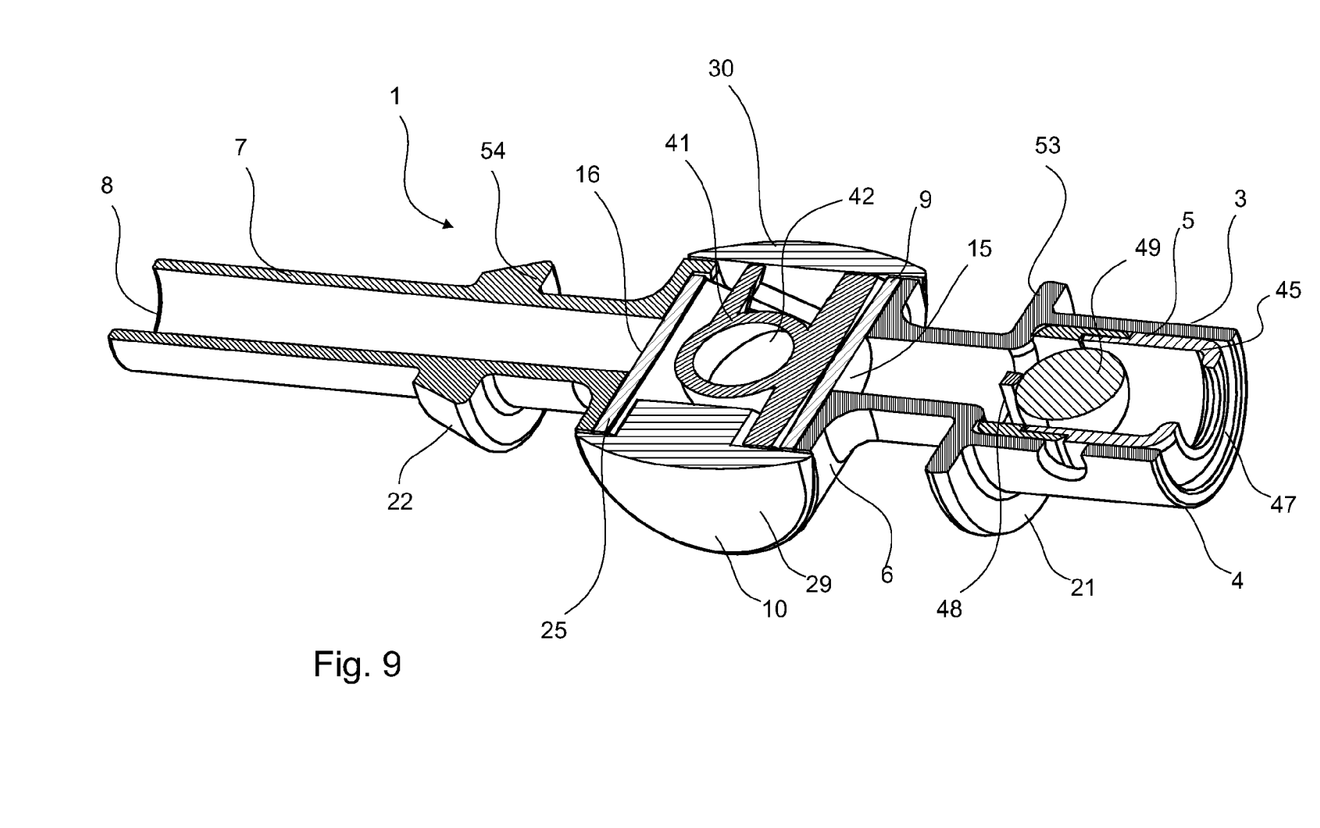
FIG. 9 is an enlarged scale, lengthwise sectional view taken along line IX-IX of the flow regulator seen in FIG. 1.
Figure 10:
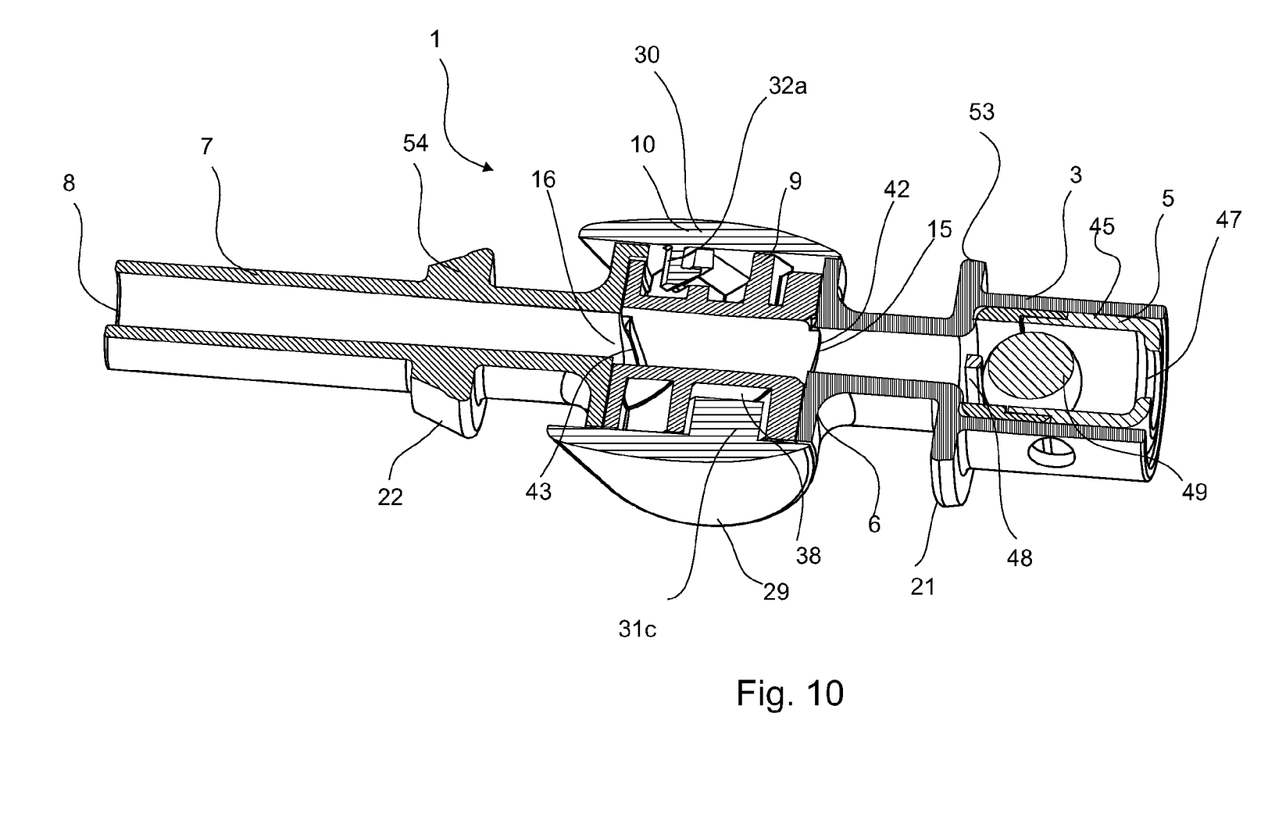
FIG. 10 is an enlarged scale, lengthwise sectional view taken along line X-X of the flow regulator seen in FIG. 1.

In FIG. 7 the interior regulator body part 9 is seen from the first interior cylinder end 26 to illustrate that the interior cylinder 24 accommodates a diametrically arranged flow pipe 41 having a first pipe opening 42 opposite a second pipe opening 43 in the interior cylinder wall 25, which second pipe opening 43 becomes aligned with the second opening 16 when the first pipe opening 42 is aligned with the first opening 15 to open the enema flow path by pivoting the pivotable grip 10 towards the tubular tube coupling end part 7, which position is seen in FIGS. 2 and 10. By pivoting the pivotable grip 10 in the opposite direction to achieve the position seen in FIGS. 1 and 9 the flow path is blocked by the interior cylinder wall 25, which are rotated in front of the second opening 16 and the first opening 15 and closes said openings 15,16.

Figure 8:
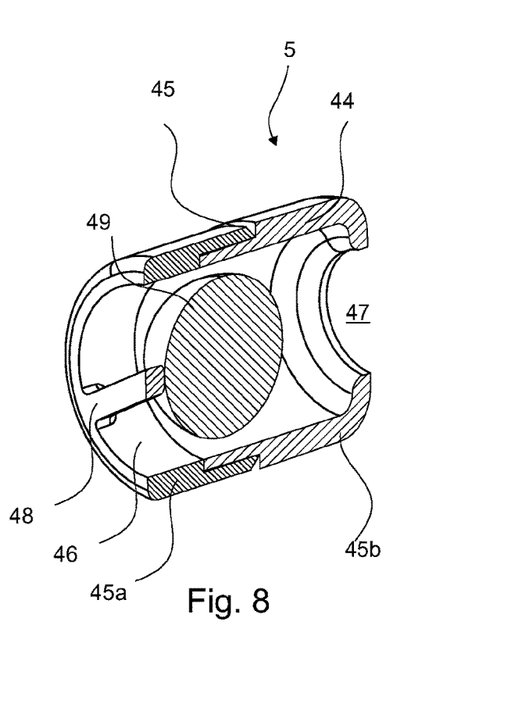
FIG. 8 is an enlarged scale, lengthwise sectional view taken along line III-III of the backflow preventer means seen in FIG. 3.
Figure 11:
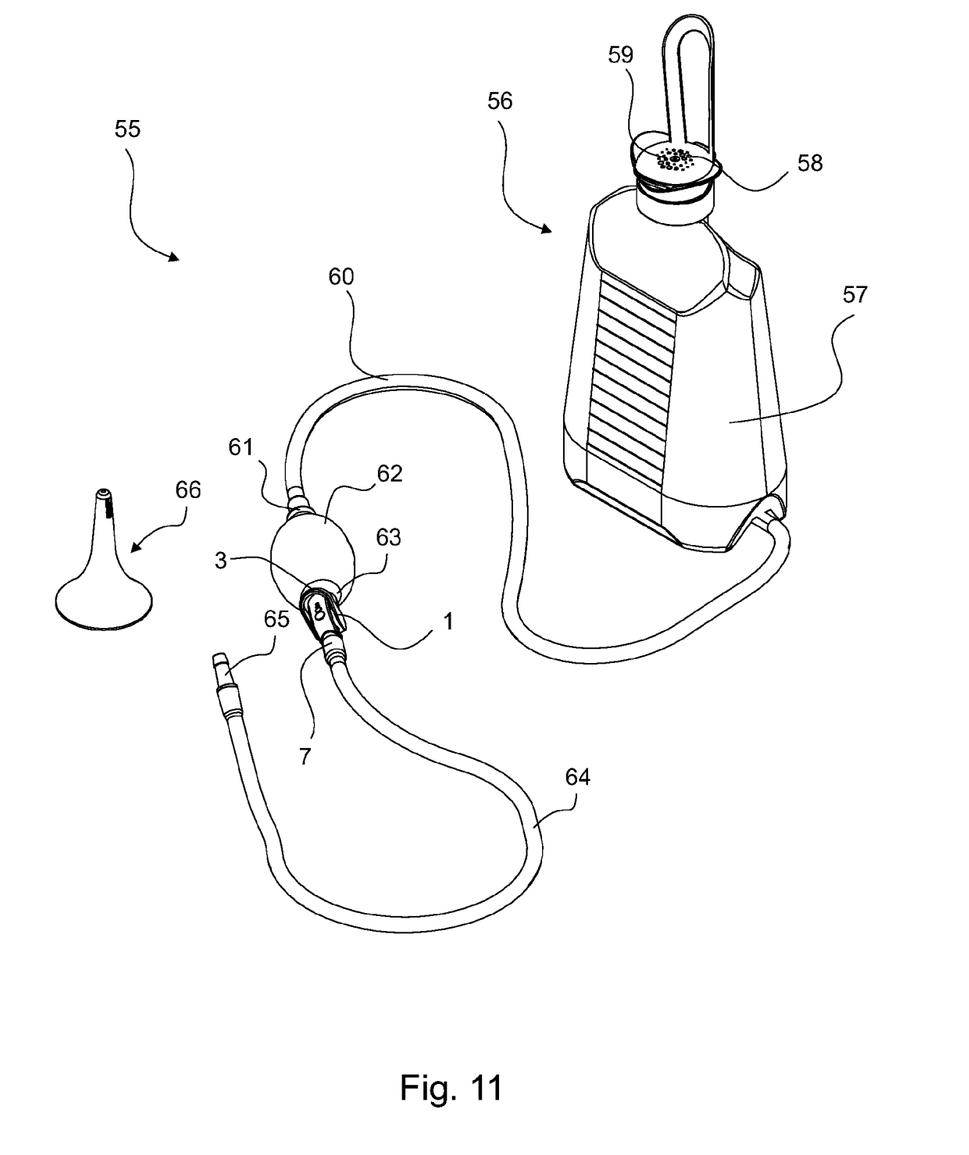
FIG. 11 is a perspective view of an enema administration system with the flow regulator seen in FIGS. 1-10.

FIG. 8 is a sectional view inside the back flow preventer 5 delimited by a circumferential valve wall 44 and being dimensioned to be situated inside the first flow section F1. The back flow preventer 5 is composed of a main valve body 45 assembled of a proximal valve body part 45a facing the free pump coupling end 4 and a distal valve body part 45b facing the first opening 15 in the inserted state. The back flow preventer 5 has an enema inlet 46, which faces the exterior regulator body 6, and an opposite enema outlet 47. The enema inlet 46 is traversed by a crossbar 48 that prevents a small valve ball 49 or bead from being sucked inside the flow regulator 1. The valve ball 49 reciprocates during squeezing and relieving pressure on an elastomeric bulb pump 62, which is seen in FIG. 11. When the elastomeric bulb pump 62 is squeezed together a negative inspiration pressure builds up thereby arranging the valve ball 49 to close the enema outlet 47 and sucking the enema into the elastomeric bulb pump 62. When the pressure is relieved the valve ball 49 returns to the crossbar 48 to allow the enema to be expelled via the enema outlet 47. The opposite end of the elastomeric bulb pump 62 has a similar back flow preventer.

Figure 6:
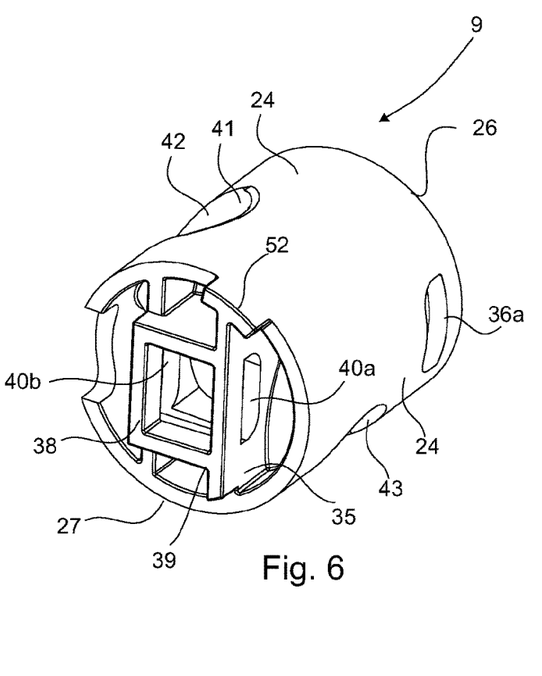
FIG. 6 is a perspective side view of the interior regulator body part seen inclined from the first interior cylinder end.

As seen in FIGS. 4 and 6 the second exterior cylinder end 14 has a first pivot stop 50 in form of an angular track 51, and the second interior cylinder end 27 has a second pivot stop 52 adapted to engage the first pivot stop 50 to restrict a pivot angle length of the pivotable grip 10.

FIGS. 9 and 10 are sectional views that illustrate the pivoted flow pipe 41 in closed and open positions, respectively. The tubular pump coupling end part 3 and the tubular tube coupling end part 7 have respective abutment collars 53,54 configured and dimensioned to arrange the elastomeric bulb pump 62 and a second tubing 64 appropriately, thus so that the flow regulator 1 is not inserted excessively into respective coupling parts 61,63 of the elastomeric bulb pump 62, and so that the second tubing 64 is mounted correctly, as seen best in FIG. 11 of the enema administration system 55 for use with the flow regulator 1.

In the present embodiment the abutment collars 53,54 are expediently constituted by the opposite bridge ends 21,22 of the bridge member 20.

The enema administration system 55 further comprises an enema reservoir 56 in form of a refillable container 57 with a hinged snap lid 58 having vent openings 59 to relieve negative pressure in response to drawing enema from said enema reservoir 56.

A first tubing 60 connects the enema reservoir 56 to an enema pump inlet part 61 of the elastomeric pump 62. An opposite enema pump outlet part 63 of the elastomeric pump 62 is coupled to the tubular pump coupling end part 3 of the flow regulator 1. The opposite tubular tube coupling end part 7 is coupled to a second tubing 64, the other end of which is equipped with a catheter coupling component 65 configured to couple to a rectal catheter 66.

In some embodiments a short length of tubing may extend the distance between the free pump coupling end part of the hand-operated flow regulator and the inspiration end of the elastomeric bulb pump, but said short length of tubing is no longer than both the elastomeric bulb pump and the flow regulator can be held and operated by one same hand. The short length of tubing has one end connected to the free pump coupling end part of the hand-operated flow regulator and its opposite end connected to a connection piece adapted to secure to the elastomeric bulb pump. The short length of tubing may e.g., have about the same length as the elastomeric bulb pump and the total length of assembled short length of tubing, flow regulator and elastomeric bulb pump may not be longer than the length of a hand.

The invention claimed is:

1. A hand-operated flow regulator adapted to be inserted between an elastomeric bulb pump and a tubing as a part of an enema flow path, the flow regulator comprising:
   a main flow body having:
      a main flow regulator axis,
      a tubular pump coupling end part having a free pump coupling end and defining a first flow section,
      the tubular pump coupling end part extends via an exterior regulator body part into a tubular tube coupling end part having a free tube coupling end and defining a second flow section, and
      an interior regulator body part is situated rotatable and substantially coaxially inside the exterior regulator body part,
   wherein the flow regulator comprises a pivotable grip in operative communication with the interior regulator body part to open and close the enema flow path,
   wherein the pivotable grip moves lengthwise along the main flow regulator axis,
   wherein the exterior regulator body part is an exterior cylinder delimited by an exterior cylinder wall and having an exterior cylinder axis substantially perpendicular to the main flow regulator axis,
   wherein the interior regulator body part is an interior cylinder delimited by an interior cylinder wall, and having an interior cylinder axis coaxially aligned with the exterior cylinder axis, and the interior cylinder has a first interior cylinder end opposite a second interior cylinder end, and
   wherein the first exterior cylinder end has a first pivot stop, and the first interior cylinder end has a second pivot stop adapted to engage the first pivot stop to restrict a pivot angle length of the pivotable grip.

2. A hand-operated flow regulator according to claim 1, wherein
   the exterior cylinder has a first exterior cylinder end opposite a second exterior cylinder end,
   the exterior cylinder wall has a first opening opposite the free pump coupling end, and a second opening opposite the free tube coupling end,
   the first opening extends into the first flow section, and the second opening extends into the second flow section.

3. A hand-operated flow regulator according to claim 2, wherein the interior cylinder accommodates a diametrically arranged flow pipe.

4. A hand-operated flow regulator according to claim 3, wherein the flow pipe has a first pipe opening opposite a second pipe opening, wherein the first pipe opening and second pipe opening are located in the interior cylinder wall.

5. A hand-operated flow regulator according to claim 4, wherein the interior cylinder is arranged inside the exterior cylinder to be pivoted between a fully open flow position in which the first pipe opening is aligned with the first opening in the exterior cylinder wall and the second pipe opening is aligned with the second opening in the exterior cylinder wall, and a fully closed position in which none of said pipe openings are aligned with any of said first opening and said second opening.

6. A hand-operated flow regulator according to claim 5, wherein a pivot angle of the pivotable grip corresponds to a rotation angle of the interior cylinder between an open position wherein a flow pipe axis of the flow pipe is fully aligned with the first opening and the second opening, and a closed position wherein said flow pipe axis is rotated so that the first pipe opening and the second pipe opening are brought fully away from the first opening and the second opening and is blocked by the exterior cylinder wall.

7. A hand-operated flow regulator according to claim 1, wherein an exterior diameter of the interior cylinder corresponds substantially to an interior diameter of the exterior cylinder.

8. A hand-operated flow regulator according to claim 1, wherein the first interior cylinder end has a first cylinder coupling means configured to lock together with a first grip coupling means of the pivotable grip.

9. A hand-operated flow regulator according to claim 8, wherein the second interior cylinder end has a second cylinder coupling means configured to lock together with a second grip coupling means of the pivotable grip.

10. A hand-operated flow regulator according to claim 9, wherein the pivotable grip has a U-bend handle part having opposite free ends provided with a respective one of the first grip coupling means and the second grip coupling means.

11. A hand-operated flow regulator according to claim 9, wherein the first grip coupling means and the second grip coupling means are male coupling means and/or female coupling means.

12. A hand-operated flow regulator according to claim 9, wherein the first cylinder coupling means and the second cylinder coupling means are female coupling means and/or male coupling means adapted to couple to the first grip coupling means and second grip coupling means, respectively.

13. A hand-operated flow regulator according to claim 9, wherein the first cylinder coupling means and the second cylinder coupling means are selected from the group comprising snap fittings, hooking means, keyways or combinations thereof.

14. A hand-operated flow regulator according to claim 9, wherein the first grip coupling means and the second grip coupling means that engage and interlock with the first cylinder coupling means and the second cylinder coupling means, respectively, are dimensioned so that the first grip coupling means covers the first interior cylinder end and the first exterior cylinder end, and the second grip coupling means covers the second interior cylinder end and the second exterior cylinder end.

15. A hand-operated flow regulator according to claim 1, wherein the first pivot stop is an angular track provided circumferentially on the first exterior cylinder end.

16. A hand-operated flow regulator according to claim 15, wherein the second pivot stop is a protrusion extending from the interior cylinder wall parallel to the exterior cylinder axis along an angular section of a circumference of the first interior cylinder end.

17. A hand-operated flow regulator according to claim 16, wherein the angular section is shorter than the angular track on the first exterior cylinder end.

18. A hand-operated flow regulator according to claim 1, further comprising a backflow preventer means.

19. A hand-operated flow regulator according to claim 18, wherein the backflow preventer means is inserted in the first flow section.

20. A hand-operated flow regulator according to claim 18, wherein the back flow preventer means accommodates a valve ball or bead, and has an enema inlet, which faces the exterior regulator body, and an opposite enema outlet, wherein the enema inlet is traversed by a crossbar configured to prevent the valve ball from being sucked inside the flow regulator.

21. A hand-operated flow regulator according to claim 18, wherein the back flow preventer means is tubular.

22. A hand-operated flow regulator according to claim 1, wherein the flow regulator has a finger support member that protrudes axially spaced apart from the main flow body along the main flow regulator axis.

23. A hand-operated flow regulator according to claim 22, wherein the finger support member is arranged with a gap to the exterior cylinder.

24. A hand-operated flow regulator according to claim 22, wherein the finger support member is arranged above the exterior regulator body part and has an exterior face having tactile indicator means.

25. A hand-operated flow regulator according to claim 24, wherein the tactile indicator means is a row of elevations.

26. A hand-operated flow regulator according to claim 25, wherein the elevations of the row of elevations have gradually reduced sizes.

27. A hand-operated flow regulator according to claim 25, wherein the elevations are disc-shaped.

28. A hand-operated flow regulator according to claim 22, wherein the finger support member is shaped as a bridge member having opposite bridge ends secured to the tubular pump coupling end part and the tubular tube coupling end part, respectively, to extend above the exterior regulator body part.

29. An enema administration system comprising an elastomeric bulb pump, an irrigation catheter, and the hand-operated flow regulator according to claim 1.

30. An enema administration system according to claim 29, wherein the free pump coupling end part of the hand-operated flow regulator is coupled directly to an inspiration end of the elastomeric bulb pump.

31. A hand-operated flow regulator adapted to be inserted between an elastomeric bulb pump and a tubing as a part of an enema flow path, the flow regulator comprising:
   a main flow body having:
      a main flow regulator axis,
      a tubular pump coupling end part having a free pump coupling end and defining a first flow section,
      the tubular pump coupling end part extends via an exterior regulator body part into a tubular tube coupling end part having a free tube coupling end and defining a second flow section, and
      an interior regulator body part is situated rotatable and substantially coaxially inside the exterior regulator body part,
wherein the flow regulator comprises a pivotable grip in operative communication with the interior regulator body part to open and close the enema flow path, wherein the pivotable grip moves lengthwise along the main flow regulator axis, and wherein the flow regulator further comprises a backflow preventer means that is inserted in the first flow section.

32. A hand-operated flow regulator adapted to be inserted between an elastomeric bulb pump and a tubing as a part of an enema flow path, the flow regulator comprising:
- a main flow body having:
  - a main flow regulator axis,
  - a tubular pump coupling end part having a free pump coupling end and defining a first flow section,
  - the tubular pump coupling end part extends via an exterior regulator body part into a tubular tube coupling end part having a free tube coupling end and defining a second flow section, and
  - an interior regulator body part is situated rotatable and substantially coaxially inside the exterior regulator body part, wherein the flow regulator comprises a pivotable grip in operative communication with the interior regulator body part to open and close the enema flow path, wherein the pivotable grip moves lengthwise along the main flow regulator axis, wherein the flow regulator has a finger support member that protrudes axially spaced apart from the main flow body along the main flow regulator axis, and wherein the finger support member is arranged with a gap to an exterior cylinder.

\* \* \* \* \*